(12) United States Patent
Fusco

(10) Patent No.: US 7,867,177 B2
(45) Date of Patent: Jan. 11, 2011

(54) METHOD FOR THE IDENTIFICATION, DIAGNOSIS AND TREATMENT OF SOMATIC DYSFUNCTIONS

(76) Inventor: Maria Antonietta Fusco, c/o KS Italia sas di Ambrosone Mario & C - Viale S. Francesco, 32 int. 138-A /sc. A, Avellino (IT) I-83100

( * ) Notice: Subject to any disclaimer, the term of this patent is extended or adjusted under 35 U.S.C. 154(b) by 433 days.

(21) Appl. No.: 11/702,772

(22) Filed: Feb. 6, 2007

(65) Prior Publication Data

US 2008/0188773 A1 Aug. 7, 2008

(51) Int. Cl.
*A61B 5/107* (2006.01)
*A61F 5/01* (2006.01)
(52) U.S. Cl. .......................................... 600/587; 600/1
(58) Field of Classification Search ........................ None
See application file for complete search history.

(56) References Cited

U.S. PATENT DOCUMENTS 6,616,619 B2 * 9/2003 Fusco .......................... 600/587

OTHER PUBLICATIONS

Dowling (JAOA. May 2000; 100(5): 285-298).*
Tiran et al. (Complementary Therapies in Clinical Practice. 2005; 11: 58-62).*
Wolfe (The Complete Idiot's Guide to Reflexology, 2006. pp. 6-7, 36, 126-127).*

* cited by examiner

*Primary Examiner*—Scott Long
(74) *Attorney, Agent, or Firm*—Steinfl & Bruno LLP

(57) ABSTRACT

A method for etiologic diagnosis of somatic dysfunctions of a patient and a therapeutic method for correction of said somatic dysfunctions, comprising the steps of identifying the presence of at least one body asymmetry or anomalous spatial arrangement while the patient is looking ahead in an erect position with relaxed shoulders; identifying at least one dynamic muscle which shows hyper-tonicity with respect to a corresponding contralateral muscle while the patient is in said position; identifying at least one peripheral receptor related to said muscular hyper-tonicity; and performing an exteroceptive, pressoceptive, and/or proprioceptive stimulation of at least one peripheral receptor identified as related to patient's somatic dysfunctions.

13 Claims, No Drawings

METHOD FOR THE IDENTIFICATION, DIAGNOSIS AND TREATMENT OF SOMATIC DYSFUNCTIONS

FIELD OF THE INVENTION

The present invention relates to a method for the identification of the pathogenesis of somatic dysfunctions and for their diagnosis and treatment.

BACKGROUND OF THE INVENTION

The expression "somatic dysfunction" indicates an altered working of the somatic system components, i.e. bones, joints, myofascial structures and relevant vascular, lymphatic and neurological elements (generally speaking, of any of the elements and structures responsible for support and locomotion). In particular, somatic dysfunctions comprise dysfunctional syndromes of the locomotor apparatus.

These dysfunctional pathologies, which are responsible for painful symptoms and functional limitations at the joints, affect an increasing part of world population and have a considerable impact from both a social and an economic point of view. Some examples of the significant incidence and effects of such pathologies onto the social and economic life are given in the following.

According to the US National Institute of Occupational Safety and Health (NIOSH), specific chronic diseases of the spinal column are the second most important health problem for workers in agriculture, industry and tertiary sector in the United States. Therefore, said diseases are to be regarded as one of the main health problems when considering both workers' pains and induced economic and social costs in terms for instance of absences for illness, therapeutic treatments, invalidities, changes of function or job.

As reported by Fordyce (Fordyce W: *Back pain, compensation, and public policy*. In: Risen J, Solomon L: Prevention and Health Psychology. Hanover, N.H. University Press of New England, 1985, pp. 127-140) in 1985 for the United States, the costs of indemnities due to permanent inability caused by lumbosacral column pathologies rose by 2700% in the period from 1956 to 1976. At present, the workers affected by chronic lumbago take up about 65-70% of the costs for indemnities, even if they represent only 10% of the whole working population. A similar trend was reported by Nachemson (Nachemson AL, Lindh M: *Measurement of abdominal and back muscle strength with and without back pain*. Scand J Reabil Med 1: pp. 60-63) for Sweden, where the costs for indemnities rose by 6000% from 1952 to 1987.

Consequently, the availability of affordable methods for the identification of the pathogenesis (i.e. for the etiologic diagnosis) of said dysfunctional pathologies and their therapeutic treatment is fundamental for both providing a relief to patient's pains and putting a curb on indemnity expenses.

Up to now, the pathogenesis of somatic dysfunctions has been generally ascribed to direct or indirect traumas of the locomotor apparatus. This approach is based on the assumption that striated muscles are able to provide the organism with both an anti-gravitational tonic function and a dynamic function at the same time. In fact, it is a general opinion that a striated muscle comprises a deep tonic component represented by myoglobin-rich red fibers and a superficial dynamic component represented by white fibers.

Following such a physiologic interpretation, the prior art diagnostic criteria for somatic dysfunctions are based on the evaluation of: (a) possible asymmetries of structural and functional parts of the musculoskeletal system; (b) mobility range of joints or musculoskeletal zones; and (c) texture of the soft tissues of the musculoskeletal system, assessed through observation and palpation tests.

Moreover, always as a consequence of said physiologic interpretation, the therapeutic treatment of somatic dysfunctions is commonly based on pharmaceutical actions mainly directed to the musculoskeletal system. In particular, anti-inflammatory and analgesic drugs are usually prescribed.

The present invention stems from the original consideration that the prior art approach exposed above presents some inconsistencies in its physiologic basis and that, consequently, the pathogenesis diagnostic criteria and the associated therapeutic treatment may have a questionable effectiveness when applied to a patient affected by somatic dysfunctions. In fact, pharmaceutical treatments are not successful in several cases and consequently the patient's pain may progressively become a chronic disease affecting wide and multi-district parts of his/her body.

The aforementioned physiologic inconsistencies detected by the Inventor are discussed in the following.

Biped and orthostatic posture of a human being is not to be regarded as a "static" and passive function, but on the contrary it results from the activation of an anti-gravitational function of the organism which is performed by a specific and specialized tissue and/or apparatus. Evidently, such a tissue and/or apparatus must be able to continuously comply with said indispensable anti-gravitational function twenty-four hours a day and therefore it requires an anaerobic metabolism without presenting metabolic acidosis and tiredness.

Moreover, the tissue and/or apparatus responsible for the anti-gravitational function must operate against shortening due to gravity force acting on the whole organism. It must also work in an automatic and involuntary manner.

Striated muscles—to which the prior art approach attributes the just mentioned anti-gravitational function—are not provided with such physical and metabolic features, neither in red fibers nor in white fibers. In fact, the activation of muscular functions consists in contraction and shortening of muscular fibers. Consequently, muscles cannot effectively contrast gravity force, since the activation of the tonic system constituted by muscular red fibers acts in the same direction of the gravity force itself.

These original observations and considerations developed by the Inventor evidence that the prior art physiologic basis of diagnosis and therapeutic treatment of somatic dysfunctions is not fully founded and that such methods need to be revised and improved in order to reach a higher diagnosis and therapeutic effectiveness.

OBJECT AND SUMMARY OF THE INVENTION

The technical problem underlying the present invention is that of providing a method for pathogenesis identification and for therapeutic treatment of somatic dysfunctions which allows overcoming the drawbacks mentioned above with reference to the prior art.

In particular, it is an object of the invention to provide an affordable method for the identification of the pathogenesis (i.e. for the etiologic diagnosis) of said dysfunctional pathologies and for their therapeutic treatment.

It is also an object of the invention to provide a method of the aforementioned type which is capable of providing a relief to patient's pains and of putting a curb on indemnity expenses.

It is a further object of the invention to provide a method is also ready and easily applicable on the field for the screening and management of large patient populations.

Such objects are achieved by a method for etiologic diagnosis of somatic dysfunctions of a patient, comprising the steps of:
- identifying the presence of at least one body asymmetry or anomalous spatial arrangement while the patient is looking ahead in an erect position with relaxed shoulders;
- identifying at least one dynamic muscle which shows hyper-tonicity with respect to a corresponding contralateral muscle while the patient is in said position, which hypertonic muscle is responsible for said at least one asymmetry or anomalous spatial arrangement; and
- identifying at least one peripheral receptor located in the patient's foot sole related to said muscular hyper-tonicity.

According to the same inventive concept, the invention also provides a therapeutic method for correction of somatic dysfunctions of a patient, based upon the above diagnostic method and comprising a step of exteroceptive, pressoceptive, and/or proprioceptive stimulation of at least one peripheral receptor located in the patient's foot sole related to patient's somatic dysfunctions.

Moreover, the present invention provides the combination of the above diagnostic and therapeutic methods.

The present invention provides some relevant advantages.

The main advantage lies in the fact that the method of the invention, which allows the identification of somatic dysfunctions and of their pathogenesis and the application of an appropriate treatment, is founded on more coherent physiologic basis than the prior art and then it is more effective.

A second advantage of the present invention lies in the fact that said diagnostic method can be carried out in a fast and simple manner, at low costs and also "on the field", in non-specialized structures.

A further advantage lies in the fact that the therapeutic method of the invention allows an effective correction of said somatic dysfunctions without the need of pharmaceutical means.

Other advantages, features and steps of the present invention will be made apparent in the detailed description of a preferred embodiment thereof, given by way of example and not for limitative purposes.

DETAILED DESCRIPTION

The diagnostic and therapeutic method of the invention moves from the original observation that the anti-gravitational function of the human body is actually carried out by elements of connective tissue, i.e. tendons, ligaments, articular capsules, intra- and extra-articular fibrous bundles, fasciae, aponeurosis, periosteum and so on.

In fact, such elements of connective tissue are set to organize and maintain the three-dimensional architecture of each joint, the roominess of thoracic, abdominal and cranial cavities and the position of internal organs inside said cavities. As an example, the fasciae connect internal organs to the musculoskeletal system.

The connective tissue can carry out a full-time anti-gravitational function, because it is not subjected to metabolic acidosis and its physical action is basically expressed as resistance to shortening; as it was previously discussed, both these necessary characteristics are instead not incorporated by muscles.

At the beginning of the 20$^{th}$ century, the neurophysiology studies of Sir Charles Scott Sherrington and co-workers (Charles Scott Sherrington: *The Integrative Action of the Nervous System*, New York, Charles Scribner's Sons, 1906. *Mammalian physiology*. Oxford and London, 1919. *The Reflex Activity of the Spinal Cord Oxford*, 1932. *The Brain and Its Mechanism*. Cambridge, 1933) demonstrated that a mammalian individual is able to hold an erect position onto a supporting surface thanks to mechanoreceptors sensitive to pressure, which are located in its extremities. In particular, the maintenance of an erect position in a human being requires the activation of specific mechanoreceptors which are sensitive to local pressure acting on foot sole skin.

On the other hand, the carrying out of the anti-gravitational function requires that the inputs from said peripheral mechanoreceptors are transmitted to the central nervous system and then to similar sensitive mechanoreceptors included in a specific tissue responsible for the implementation of such a function. It should be noted that the connective tissue is the only internal tissue provided with mechanoreceptors sensitive to pressure and traction likewise mechanoreceptors in skin. Therefore, this is a further element in confirmation of the abovementioned interpretation of the Inventor.

More in detail, the human posture results from two main functions: (i) supporting head and body against gravity force and further external forces; and (ii) maintaining the vertical projection of body center of gravity within the support base on the ground.

In a static erect position, the head is maintained in a vertical position through the activation of vestibular-cervical and vestibular-spinal reflexes, while cervical and vestibular reflexes act on the neck in a synergic way and on limbs in an antagonist way. Exteroceptive, pressoceptive, and proprioceptive inputs originating in mechanoreceptors in foot sole and visual sensitive inputs about the orientation with respect to the horizon line are also important in order to carry out an effective and coherent anti-gravitational action, as already mentioned above.

An alteration in the anti-gravitational function can be pointed out by the presence of body asymmetries, of anomalous spatial arrangements of joints and/or of dynamic muscles in chronic and asymmetric contraction. In fact, these occurrences indicate that the connective tissue system is not able to self-sufficiently perform the anti-gravitational function in a correct way and therefore that a part of said function is empowered to dynamic muscles which work as auxiliary anti-gravitational system to maintain orthostasis.

However, orthostasis maintained through connective tissue system alone is physiologic, economical, and non-symptomatic, while, on the contrary, orthostasis maintained with the help of auxiliary dynamic muscles is non-physiologic, energy-consuming and gives rise to structural modifications of the organism three-dimensional architecture and to pains at the joints and muscles.

Said orthostatic dysfunctions can be due either to organic reasons, such as anatomic or histologic modifications of the musculoskeletal structure and in particular of the associated connective tissue, or to functional dysfunctions leading to a bad-working musculoskeletal structure, even if the latter is sound from an anatomic and histologic point of view. In this second case, somatic dysfunctions are due to bad neuroreceptive information from extremities rather than to direct or indirect traumas of the locomotor apparatus.

Therefore, when body asymmetries not related to organic diseases of the musculoskeletal structure are encountered, these can be ascribed to upset peripheral receptive information, i.e. to non-univocal and inconsistent inputs coming to the central nervous system from peripheral mechanoreceptors as for instance exteroceptive and proprioceptive systems in foot sole. Bad working of these receptors causes a disorder in receptive information and consequently a disorder also in muscular and ligamental tensions, so leading to asymmetries.

In light of the former explanation, pain associated with non-organic somatic dysfunctions has a mechanic origin due to an anomalous extension of tissues and their nerve endings, rather than an inflammatory origin accompanied by common chemical-originated phenomena as reddening, warming, swelling and so on. Pain with mechanical origin is not very sensible to anti-inflammatory and analgesic drugs, since there is no chemical feature on which such drugs may act.

Moving from the physiologic elements given in the preceding, a method for the etiologic diagnosis of somatic dysfunctions of a patient according to the present invention comprises a step of asking the patient to stand up in his/her most comfortable position. More specifically, he/she should look ahead while maintaining an erect position with relaxed shoulders. In a perfectly regular condition, a similar biped and orthostatic posture should be maintained through the activation of anti-gravitational vertical stabilization system only, whereas no system specific for dynamic purpose should be activated for said vertical stabilization purpose.

A subsequent step of the present etiologic diagnosis method comprises the identification of body asymmetries or anomalous spatial arrangements of the patient, since these are symptoms of somatic dysfunctions.

If the patient is not affected by organic diseases as anatomic or histologic diseases of the musculoskeletal structure, one or more dynamic muscles in hyper-tonicity with respect to the tone of corresponding contralateral muscles can be identified as causing such asymmetries or anomalous spatial arrangements.

For instance, an asymmetry of the scapular cingolum appearing as a shoulder higher than the contralateral one would be caused by a hyper-tonicity of trapezius homologous to the higher shoulder. In such a case we can assume that said trapezius is hyper-tonic because it is assisting a vertical stabilization system which is non-properly carrying out its anti-gravitational function. Similarly, when the patient is not in motion and no organic disease is found, all chronic contractions and/or hyper-tonicity conditions of only one side of paired dynamic muscles denote a functional modification of the vertical stabilization system.

A successive step of the etiologic diagnosis method according to the present invention comprises the identification of one or more specific peripheral receptors which are related to said hyper-tonicity of said one or more dynamic muscles, which one or more specific receptors are to be searched in the patient's foot sole.

Following the description above, the peripheral receptors to be identified are those whose bad working is responsible for non-univocal and inconsistent inputs and a disorder in the receptive information transmitted to the central nervous system, so leading to a disorder also in muscular and ligamental tensions.

In order to assess the functionality of the sensorial connections coming from the peripheral receptors, the following methodology is preferably used.

The Inventor's approach provides for an evaluation of the foot sole while the patient is in a lying position, preferably employing the deltoid as sample muscle.

Small material pieces, preferably of cork and of thickness not greater than 2 mm and an area of about 4-5 $mm^2$, are applied at selected spots under the foot sole, and specifically one foot at a time and one piece at a time.

The starting point of the sensorial connections is thus identified as the one producing a contraction in the sample muscle.

The fact that the evaluation is carried out in said lying position allows excluding from the assessment the pressure-sensitive receptors located at the foot sole.

According to a further preferred feature of the Inventor's approach, the pressure to apply at each spot of the foot sole is carefully selected and generally speaking it is a mild touching, similar to a light brushing, in order not to distort the reaction of the sample muscle.

Moreover, always according to the Inventors' approach, the spots under the foot sole are preferably selected in a group comprising:
flexor hallucis brevis,
adductor hallucis,
flexor digiti quinti brevis,
abductor hallucis,
abductor digiti quinti,
cuneous pronator, and
cuneous supinator.

The therapeutic method of the invention will now be described.

This method consists in a therapeutic treatment for somatic dysfunctions directed to the correction of disorders in receptive information coming from said peripheral receptors. In particular—and consistently with the above—said therapeutic treatment is directed to the peripheral receptors located in the foot sole.

The therapeutic method which is object of the present invention comprises exteroceptive, pressoceptive, and/or proprioceptive stimulation of said peripheral receptors, preferably performed at the spots listed above.

The therapeutic method is based upon the use of a specific therapeutic means, namely a foot insole having stimulation means arranged at said selected spots under the foot sole.

The insole is preferably made of a layer of natural caoutchouc and by a layer of alcantara.

Said stimulation means comprises seven alveoli, bulges or pockets, each arranged at a respective stimulation spot corresponding to muscle insertion regions of specific intrinsic muscles. The location of the stimulation means can of course be adapted to each specific therapeutic need.

Preferably, the insole has pre-arranged pockets that can be selectively filled according to each patient's specific need. In this respect, after identifying the disturbed peripheral receptor, the stimulation at the identified region is activated by filling up the respective pocked.

Alternatively, the insole may have pre-filled elastic bulges.

Preferably, an elastic material is used for filling the alveoli or bulges, and in particular the material known with the commercial name of BIOTENS® can be used.

Preferably, the selected material is capable of developing, with a 4 mm thickness, an elastic force equal to the pressure force acting thereupon (Hooke Law of 1676, *"ut tensio, sic vis"*.)

Preferably, the filling material is capable of developing an isotropic elastic force.

The specific elastic force to be exerted can also be selected so that either only the cutaneous mechanoceptors are stimulated, therefore having only an antalgic response, or also, with greater pressures, the articular and muscular proprioceptors are stimulated, in order to have also a re-alignment of the somatic system.

The foot insole just described acts as a neuroceptorial stimulator, as it is able to exert a continuous, substantially vertically-directed massage under the foot sole, actively stimulating the extension muscles of the whole human body.

The insole acts as a preferential interface with the nervous system so as to correct deficiencies thereof.

The therapeutic approach of the Inventor provides for an interaction with the peripheral skin terminations of the foot sole in such a way that the therapeutic means is indeed perceived by the human body as an integral part of its intrinsic biologic system. The proposed approach is well tolerated also by an aching, arthrosic or arthritic foot and provides for a therapeutic means which does not create an excessive bulk in the shoes.

Moreover, according to the preferred features thereof mentioned above, said therapeutic means is also nice to see and to touch.

The stimulation of peripheral receptors according to the invention leads to restoration of regular anti-gravitational system functionality and then removes body asymmetries and muscular hyper-tonicity conditions.

It will be appreciated at this point that a combination of the described method for etiologic diagnosis of somatic dysfunctions of a patient together with said therapeutic method for correction of them provides means for identification and treatment of said dysfunctions.

The present invention has been hereto described with reference to a preferred embodiment thereof. It is understood that other embodiments might exist, all falling within the concept of the same invention, and all comprised within the protective scope of the appended claims.

The invention claimed is:

1. A method for the etiologic diagnosis of somatic dysfunctions in a patient, comprising the steps of:
    (a) identifying the presence of at least one body asymmetry or anomalous spatial arrangement while the patient is looking ahead in an erect position with relaxed shoulders;
    (b) identifying at least one dynamic muscle which shows hyper-tonicity with respect to a corresponding contralateral muscle while the patient is in said position, which hypertonic muscle is responsible for said at least one asymmetry or anomalous spatial arrangement; and
    (c) identifying at least one peripheral receptor located in the patient's foot sole related to said muscular hyper-tonicity,
    wherein said step (c) is performed by applying material pieces at selected spots of the foot sole, one foot at a time and one piece at a time, while observing a possible consequent contraction of a sample muscle.

2. The method of claim 1, wherein said step (c) is performed with the patient in a lying position.

3. The method of claim 1, wherein said sample muscle is the deltoid.

4. The method of claim 1, wherein said spots are selected form a group consisting of: flexor hallucis brevis, adductor hallucis, flexor digiti quinti brevis, abductor hallucis, abductor digiti quinti, cuneous pronator, and cuneous supinator.

5. The method of claim 1, further comprising a step of exteroceptive, pressoceptive, and/or proprioceptive stimulation of at least one peripheral receptor located in the patient's foot sole based on the diagnosed muscular hyper-tonicity.

6. The method of claim 5, wherein said stimulation is carried out by a foot insole having elastic bulges at selected spots under the foot sole.

7. The method of claim 1, wherein the material pieces are made of cork.

8. The method of claim 1, wherein a thickness of the material pieces are not greater than 2 mm, and an area of about 4-5 $mm^2$.

9. The method of claim 1, further comprising the steps of:
    selecting specific spots of the foot sole; and
    mildly touching the specifically selected spots of the foot sole,
    wherein the mild touching permits undistorted reaction of the sample muscle.

10. The method of claim 9, wherein a starting point of sensorial connections is identified as the spots of the foot sole that produces a contraction in the sample muscle.

11. The method of claim 1, wherein the patient is free of organic diseases.

12. The method of claim 1, wherein the method is capable of being conducted on-the-field.

13. The method of claim 1, wherein the at least one body asymmetry is one scapular cingolum being higher than a contralateral scapular cingolum.

* * * * *